US008237789B2

(12) United States Patent
Maehringer-Kunz et al.

(10) Patent No.: US 8,237,789 B2
(45) Date of Patent: Aug. 7, 2012

(54) AUTOMATIC INSPECTION DEVICE FOR STENTS, AND METHOD OF AUTOMATIC INSPECTION

(75) Inventors: Edgar Maehringer-Kunz, Muenster-Sarmsheim (DE); Matthias Loeffler, Eisenberg (DE); Reinhard Rode, Heilbronn (DE); Tanja Schneider, Floersheim (DE); Gerald Jarschel, Egelsbach (DE); Kathrin Eggelbusch, Mainz (DE)

(73) Assignee: IMSTec GmbH, Mainz (DE)

( * ) Notice: Subject to any disclaimer, the term of this patent is extended or adjusted under 35 U.S.C. 154(b) by 1150 days.

(21) Appl. No.: 11/991,414

(22) PCT Filed: Aug. 30, 2006

(86) PCT No.: PCT/EP2006/065814
§ 371 (c)(1),
(2), (4) Date: Apr. 14, 2008

(87) PCT Pub. No.: WO2007/025986
PCT Pub. Date: Mar. 8, 2007

(65) Prior Publication Data
US 2009/0251535 A1    Oct. 8, 2009

(30) Foreign Application Priority Data
Sep. 1, 2005  (DE) ............... 20 2005 013 876 U

(51) Int. Cl.
H04N 7/18  (2006.01)
(52) U.S. Cl. ............... 348/92; 348/89; 382/152

(58) Field of Classification Search ............... 348/86, 348/92, 89; 382/152
See application file for complete search history.

(56) References Cited

U.S. PATENT DOCUMENTS

| 4,815,844 | A | 3/1989 | Schmalfuss et al. |
| 6,606,403 | B2 | 8/2003 | Freifeld |
| 6,618,136 | B1 | 9/2003 | Ishida |
| 7,815,624 | B2 * | 10/2010 | Larson ............... 604/523 |
| 2003/0192914 | A1 | 10/2003 | Morita et al. |
| 2005/0151979 | A1 | 7/2005 | Sickmeyer |
| 2005/0168729 | A1 * | 8/2005 | Jung et al. ............... 356/237.2 |
| 2005/0278070 | A1 * | 12/2005 | Bash et al. ............... 700/276 |

FOREIGN PATENT DOCUMENTS

| DE | 4128856 A1 | 3/1993 |
| DE | 10356765 | 7/2005 |
| EP | 0 249 799 | 12/1987 |
| EP | 0 660 098 | 6/1995 |
| JP | 2001066521 | 3/2001 |
| JP | 2001070455 | 3/2001 |
| JP | 2001074433 | 3/2001 |

OTHER PUBLICATIONS

Search report dated Sep. 1, 2005 for underlying International PCT Application No. PCT/EP2006/065814.

* cited by examiner

Primary Examiner — Viet Vu
(74) Attorney, Agent, or Firm — Cozen O'Connor

(57) ABSTRACT

A device for automatic illumination and inspection of tubular probes, in particular stents, is proposed, with rotatable means for holding the probes that are to be inspected, with an electronic camera and associated lens, with a computer-based electronic imaging system, and with means for illuminating the probe that is to be inspected. The probe surfaces are illuminated by means of a combination of dark field illumination and transillumination.

46 Claims, 5 Drawing Sheets

AUTOMATIC INSPECTION DEVICE FOR STENTS, AND METHOD OF AUTOMATIC INSPECTION

FIELD OF THE INVENTION

The present invention pertains generally to an automatic device for illuminating and inspecting objects such as cardiovascular stents and other small, precision-cut tubes and components.

BACKGROUND OF THE INVENTION

Stents are fine, cylindrical pieces of wire mesh, which are introduced into arteries in which deposits have formed. A balloon catheter is then used to expand the stent at the narrowed point of the artery. After the catheter is removed, the stent serves as a vascular support, which keeps the artery open. Depending on the individual situation and the area of application, stents can be designed in different ways, different sizes, and can be made of different materials, including their coatings.

Cardiovascular stents must meet stringent requirements to ensure that they will function properly. If the stent has rough or sharp edges, it can damage blood cells or the blood vessels into which they are inserted. This can lead to further rupture of the atherosclerotic plaque, embolisms, and blood clots, which can lead in turn to potentially life-threatening situations.

The present invention pertains to a device for illuminating and inspecting stents and other similar parts which have the form of small, precision-made tubes.

Lasers are usually used to cut or weld stents. Although highly precise, such a method can occasionally lead to defective parts. Stents are relatively small with diameters of only about 1 mm. After processing, the individually cut features on a stent range from 50 to 200 μm in size. Accordingly, small changes in the process parameters such as the laser power, tube diameter, etc, can cause defects. Such defects can include a feature having a size that is out-of-tolerance or a feature that is malformed.

Because stents are used in the heart or in other critical areas of the circulatory system, a malfunction of the stent can be life-threatening. The production of stents therefore typically includes inspection measures. Normally, a human operator examines the stents under a stereo microscope to determine if there are any visible defects. The cylindrical stent is rotated by means of an appropriate mechanical device, and the operator inspects both the inside and the outside of the stent, section by section. Typical defects include, for example, deviations of the stent structures from the nominal dimensions and various kinds of surface defects, such as contamination, scratches, sharp points, etc., the elimination of which are absolutely critical to the safe functioning of the stent. A multi-dimensional inspection is typically conducted by a human operator with the use of a profile projector. Alternatively, this examination can also be conducted automatically using an image processing system.

Many problems are associated with such manual and automatic inspection methods. First, human error makes the visual inspection of products less effective. Second, manual inspection is relatively slow and, thus, represents a relatively expensive side of the production process. Furthermore, a typical profile projector used for manual inspection does not usually supply numerical dimensional data, which could be important under certain conditions for process control. In addition, when the outer and inner surfaces of the stent are examined, typically both surfaces are illuminated simultaneously. This leads to reflections, which prevent automatic inspection.

JP 2001066521 A describes a method and a device for inspecting the inside surface of a (coated) stent, according to which the stent is pushed onto a so-called "fiber scope". The inspection is conducted visually by an observer. It is therefore not automated. However, there is nothing in this publication with respect to how the stent is illuminated.

JP 2001070455 A discloses a method for inspecting the pattern width on the surface of the stent. The recorded image of the stent is compared with previously entered reference data.

This document also fails to provide any information on how the stent is illuminated.

JP 2001074433 A describes a method and a device similar to JP 2001070455 A for inspecting the outside surface of a stent. No illumination is provided for the stent during inspection.

Lastly, U.S. Pat. No. 6,606,403 B2 discloses an automatic system for illuminating, inspecting, and measuring stents and other small, precision-cut tubes and components. The system disclosed therein consists of a linear array electronic camera with a lens; a light source for providing the necessary illumination; a mandrel onto which the tube is mounted during the inspection; a rotating stage for rotating the mandrel; and a computer-based electronic image-recognition system, which creates a line-by-line image of the stent as it rotates under the camera. This system, however, can only be used to inspect the outside surface of the stent.

SUMMARY OF THE INVENTION

An object of the present invention is to therefore provide a device which makes it possible to inspect both the inside and the outside surfaces of a stent quickly and automatically so that defects in the contour and surface of the stent can be detected.

Another object of the present invention is to provide illumination for the surface of the object to be examined which makes it possible to conduct automatic inspection with a high level of precision.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention is described in greater detail below on the basis of the drawings.

DETAILED DESCRIPTION OF AN EXEMPLARY EMBODIMENT

Figure 1:
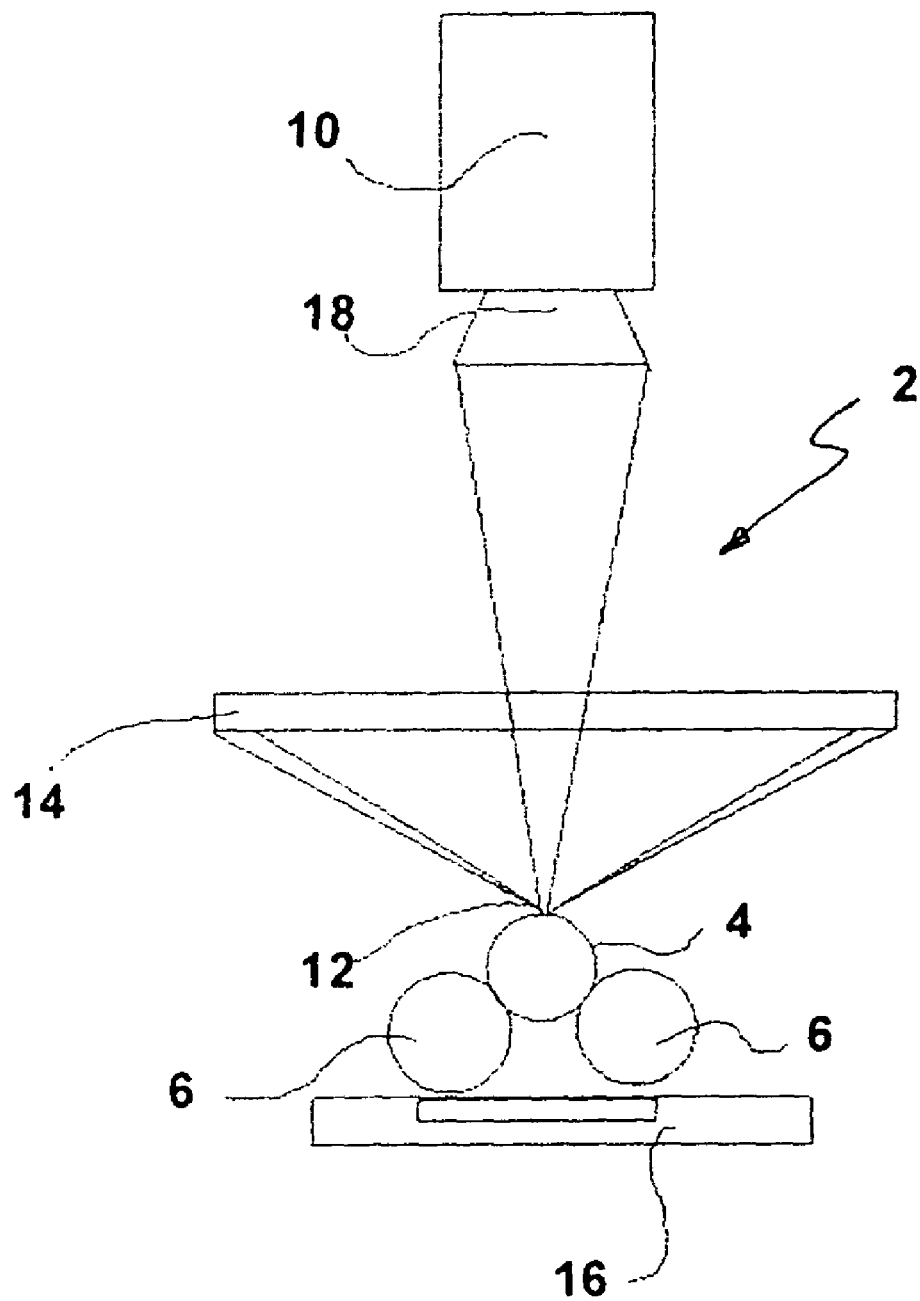
FIG. 1 shows a schematic diagram of the design of the inventive device.

In the following, the invention is explained in greater detail on the basis of the attached drawings, which illustrate an example of the inspection of a stent. The skilled person will readily appreciate that the inventive device is not limited to the illumination and inspection of stents but rather can also be applied to a wide variety of tubular objects. In addition, the skilled person will readily appreciate that the inventive device can also be used to inspect both uncoated and coated samples.

As previously mentioned, cardiovascular stents are permanently placed in a blood vessel to serve as scaffolding to keep an occluded artery open. In use, stents are inserted into the artery on a catheter and typically deployed by the inflation of a very small balloon at the end of the catheter on which the stent is mounted.

As part of the process of producing stents in this manner, the stents must be carefully checked for defects. During this inspection, both the inside and the outside surface of the stent must be examined. The basic difficulty, however, is to provide a method of illumination which makes it possible to selectively illuminate either the outside or the inside surface within a limited range. If both sides are illuminated simultaneously, stray reflections occur, which prevent precise automatic inspection of the stent.

When tubular samples, such as cardiovascular stents are examined using conventional methods, they are placed on two rotating guide rollers. As a result, it becomes possible to turn the stent to any position such that it can be examined from all sides. The inspection is conducted under external illumination; that is, the outside and the inside surfaces are illuminated simultaneously. The outside and inside surfaces of the stent are thus brought into focus one after the other, and the stent is inspected. Because of the simultaneous illumination of both surfaces, images with very strong stray reflections are obtained. This makes it difficult, however, to conduct reproducible manual inspection and prevents automatic inspection based on the use of image-processing algorithms.

In the present invention, the surfaces of the object are illuminated by a combination of dark-field illumination and transmittent illumination. In the case of the dark-field illumination, which, for example, can be accomplished by illumination with a ring light, direct light without an object does not arrive at the lens. Only through the presence of a structured object with edges will the light be scattered and thus be visible against the dark background.

To increase the contrast of the image of the stent contour, a transillumination unit 16 is set up opposite the camera 10 to form an image of the stent 4 as a dark object against a bright background. This offers optimal segmentation possibilities. The prerequisite for optimal segmentation in image processing is the highest possible contrast between the area of interest and the environment. The use of light from the transillumination unit 16 leads to an optimal contrast level, because here only the shadowing effect of the stent structures to be examined is important. The transmittent illumination can be realized with, for example, an electroluminescent panel. However, there are other ways to achieve the desired transmittent illumination, such as an optical waveguide with a lens mounted in front, a ring light, etc.

FIG. 1 shows a schematic diagram of the configuration of the inventive device 2.

Here, the stent 4 is "unwound" in front of the camera 10 with an appropriate lens by means of a rotating device consisting of two parallel rollers 6 to avoid errors in the optical imaging of the stent surface. The camera can be, for example, a linear array camera, a CCD camera, a matrix camera, etc. The lens system is designed so that it tolerates variations in the stent surface (form deviation) or deals with them with an autofocus system. Moreover, when the inside surface of the stent is being inspected, the outside surface of the stent is specifically situated as far away as necessary from the focal area. During an inspection, the apex 12 of the stent 4 is normally at the image focal point during the imaging of both the inside and the outside surface.

In accordance with the above described embodiment, the means 6 used to rotate the stent consists of two parallel rollers. In accordance with another advantageous embodiment, the stent can be rotated under the camera arrangement without slippage by gripping it at the ends from the inside or from the outside and then rotating it. This can be achieved, for example, by the use of cones, with a respective single cone being mounted in each end of the stent. Here, a number of pins, such as three pins spaced 120° apart, are provided on the cones. The pins then engage the end surfaces of the stent and rotate it. In another advantageous embodiment, the contacting which occurs when the end surfaces are gripped is discontinuous, that is, by a cone with n×3 pins spaced apart by 120°/n. Here, the term "discontinuous" means that the contact point between the gripping device at the end surfaces of the stent and the stent itself does not always remain the same during the rotation but rather is varied in a desired manner. Thus, for example, the contact points are not always at the same location on the end surfaces on or inside the stent, so that the entire surface of the stent is freely available for inspection at a given time, without the contacting components covering any part of the stent, which could not therefore be inspected.

In another application, the lateral surfaces (e.g., cut edges, cut surfaces, welded edges and surfaces) of the stent 4 are also inspected. For this purpose, the previously described optical arrangement can be positioned relative to the surfaces to be inspected as necessary.

Figure 4:
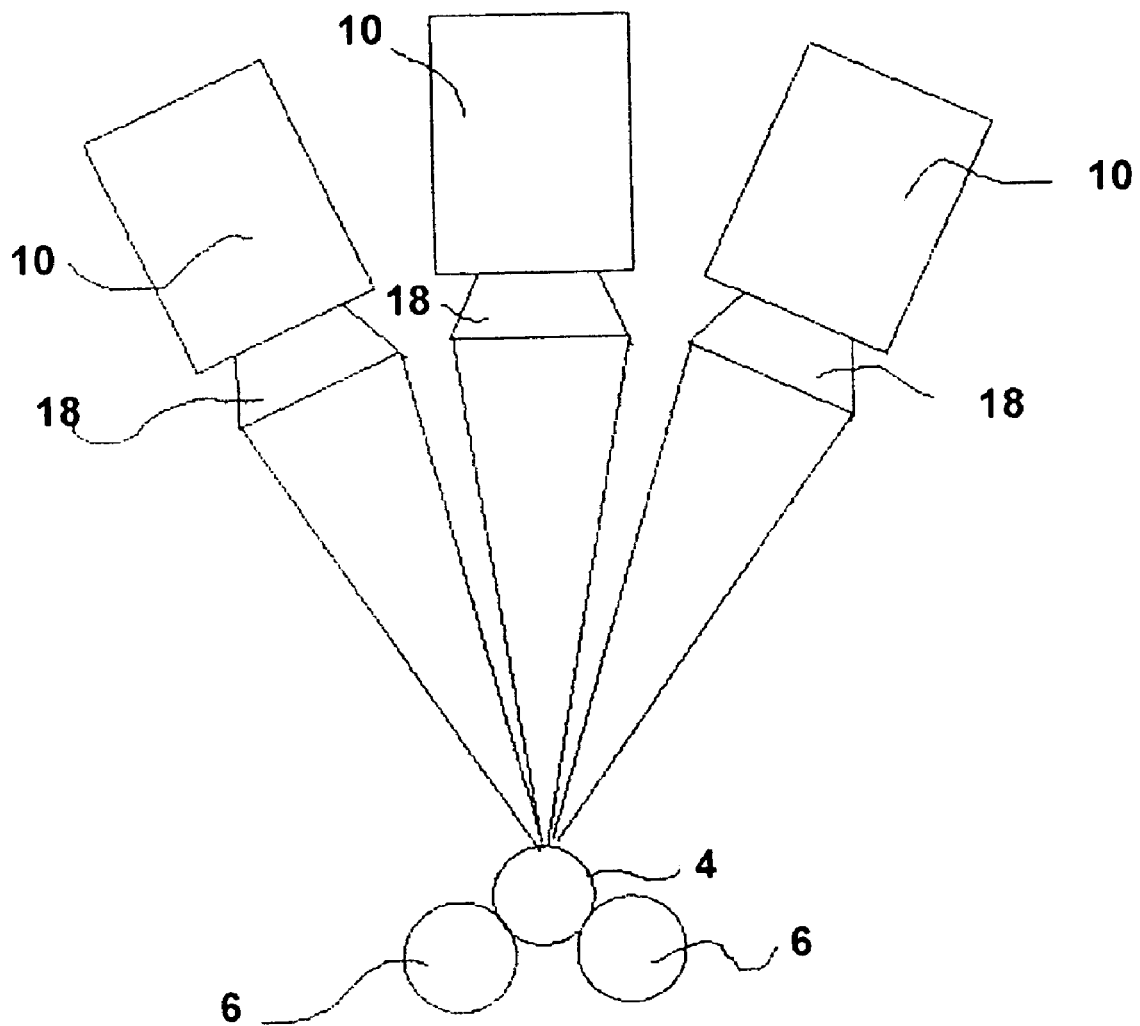
FIG. 4 show a schematic diagram of the use of a plurality of inventive devices.

In another exemplary embodiment of the inventive device, a series of optical arrangements are arranged in parallel and used for inspection of the stent (see FIG. 4).

Figures 5A, 5B:
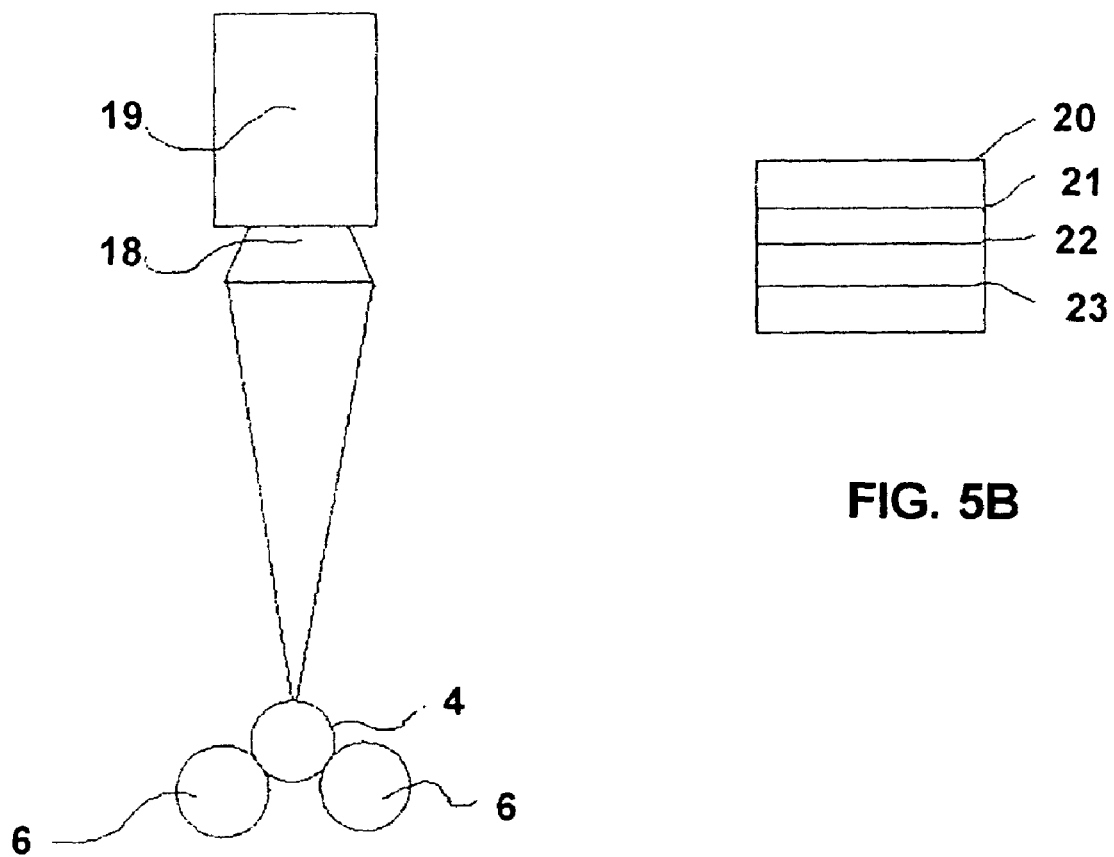
FIGS. 5A and 5B show schematic diagrams of the use of a matrix camera in the inventive device.

In another advantageous embodiment of the inventive device, a matrix camera 19 is used to image the surfaces to be examined (see FIG. 5A). For each of the desired subsections (e.g., surface, edges, etc.), the data are read out line by line from the matrix camera 19 (20-23 in FIG. 5B). As the process is repeated, a complete image is thus obtained for each subsection of the stent.

The surface of the object is illuminated, for example, with the help of a ring light 14, the distance between the ring and the apex of the stent and radiation characteristics of which create a "dark field". As a result, the edges of the stent webs produced by laser processing stand out as bright lines in the recorded image. Possible defects such as scratches, bumps, etc., on the otherwise smooth surface of the webs generate bright reflections against the dark background in the optical image. Both the stent contours and the surface defects are then automatically recognized and evaluated by means of the image-processing algorithms. Dark-field illumination is also helpful because of the highly reflective or mirror-like surface of the stent (resulting from the electropolishing process used during production). Naturally, it will be appreciated that other possibilities of dark-field illumination are also possible, such as, by one or more optical waveguides with lenses in front, which are oriented at a shallow angle to the surface of the sample.

In another advantageous embodiment, an incident (vertical) illumination system (e.g., a ring light, coaxial illumination, etc) is also used to increase the optical contrast of surface defects which do not have a pronounced edge structure.

In the previously described type of automated inspection, two-dimensional image data are obtained; that is, when an edge is detected (e.g., the edge of a defect), it is impossible initially to differentiate between an elevation (ridge) and a depression (hole). In some applications, however, such differentiation is extremely important so that a deviation which can be tolerated can be distinguished from one which cannot.

In another advantageous embodiment of the inventive device, therefore, the ring segment of the stent detected as part of the two-dimensional optical inspection is sent to a topographical sensor (e.g., a confocal sensor, an interferometer, etc.). By means of the selective scanning of the sample surface in the area of the deviation previously detected in the two-dimensional image, a signal is obtained from which the required elevation information can be extracted. The advantage of the combination of measurement methods described herein is that it limits the use of the highly precise and, thus, more time-consuming topography sensor to the area of the sample surface which has been preselected by means of the rapid two-dimensional optical measurement.

Depending on the type of defect which is present, e.g., residual material, different wavelength regions of the light used for illumination will be reflected or absorbed to different degrees. Through the use of filters to transmit the light reflected or absorbed to a greater degree by the defect which is present, the contrast in the optical image required for evaluation can be obtained.

To determine the deviation of the actual structure from the nominal structure of the stent webs, CAD data used for the production of the webs by laser cutting can be entered into the inspection software and then used as reference data. As a result, it becomes possible to adapt the contemplated embodiments of the device to new stent designs and dimensions without the need to teach the system the new structures as would otherwise be necessary with the conventional methods.

The automated inspection of the stent interior, which was not realizable according to the previous prior art, is achieved in accordance with the contemplated embodiment of the inventive inspection device 2 by the combination of the holder for the stent and an appropriately adapted optical imaging system.

Figure 2:
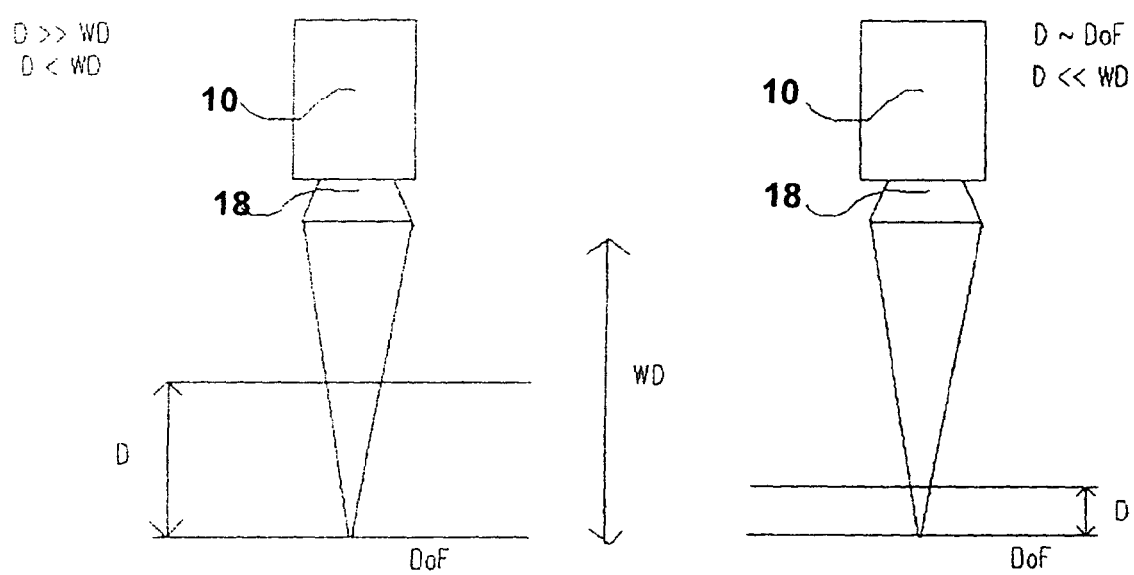
FIG. 2 shows a schematic diagram of the principle of the inventive device.

FIG. 2 shows the principle used to obtain images of the inside surface of the stent. Through the use of an optical system consisting of a microscope objective 18 with magnification V, a numerical aperture NA, a working distance WD, and a depth of focus DoF, the situation shown on the left of the figure is realized. The depth of focus of the objective 18 is small in comparison to the diameter D of the stent 4, that is, in comparison to the distance between the inside and the outside. The numerical aperture of the objective 18 is selected or adjusted such that the resulting focal depth range is sufficient to image the variations in the surface (e.g., variations in height) relative to the lens system. Simultaneously, the focal depth range is set as low as possible to mask out the stent structures lying above during the inspection of the inside surface (see FIG. 2). Depending on the type and position of these stent structures, the space frequencies, that is, the angular components of the optical image, will be blocked or scattered to differing degrees, which leads in the resulting overall image to a lack of focus. It is possible to compensate for such a lack of focus by subsequent image processing.

To achieve a high-quality image of the inside surface of the stent, which is a prerequisite for any type of automatic inspection, the previously mentioned holder for the stent 4 is also important. In the case of the prior art described above, the stents are placed on mandrels, which must also be adapted to the diameter of the stent in question. When the stent is supported in this way, the inside surface is not freely accessible optically, nor is it easy to design an automatic loading system.

Figure 3:
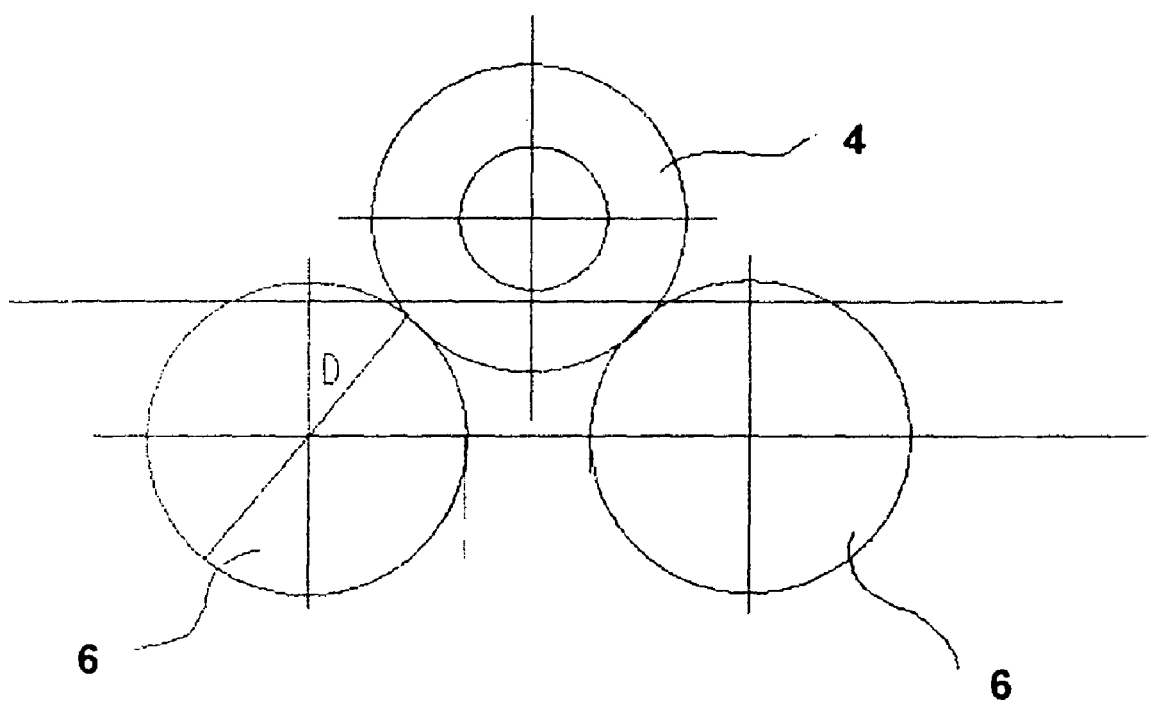
FIG. 3 shows a schematic diagram of the holder for the sample to be examined.

With the holder for the stents 4 shown in FIG. 3, which uses two parallel rollers 6, optimal conditions are obtained for imaging the inside surface of the stent; that is, the holder exerts no effect on the light used for illumination or on the guidance of the reflected components of this light. The roller diameters D are as small as possible, i.e., comparable to the diameters of the stents. In contrast to the spindles according to the prior art, however, a single set of rollers can be used for all standard stent diameters. The gap between the rollers 6 can be adjusted automatically and adapted to the stent diameter such that geometric variations of the stent 4 or the rollers 6 exert minimal effect on the focal plane of the optical system. With this design of the stent holder and of the rotation system, it becomes possible to support the inside surface of the stent at the highest possible point in space above the rollers 6.

In another advantageous embodiment of the inventive device, suitable means are used to provide the rollers 6 with an appropriate coefficient of friction to avoid slippage between the stent 4 and the rollers. For example, the rollers can be structured or coated, that is, with a layer of material applied in a structured form, e.g., a grid structure, etc.

In another advantageous embodiment of the invention, the surfaces of the rollers are structured such that a positive connection is established between the stent 4 and the rollers 6 to avoid slippage between the stent 4 and the rollers 6.

In an other advantageous embodiment of the invention, the rollers 6 are rotated at different angular velocities to avoid slippage between the stent 4 and the rollers 6.

In yet another advantageous embodiment of the invention, externally applied negative pressure is used to draw the stents 4 onto the surface of the rollers to avoid slippage between the stent 4 and the rollers 6.

In yet another advantageous embodiment of the invention, external suction is used to avoid slippage between the stent 4 and the rollers 6.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device for the automatic illumination and inspection of tubular samples, comprising:
   rotatable means for holding the tubular samples to be inspected;
   an electronic camera with an associated lens system;
   a computer-based electronic image-processing system; and
   means for illuminating a tubular sample to be inspected;

wherein the surfaces of the tubular sample are illuminated simultaneously by a combination of dark-field illumination and transmittent illumination,
wherein the means for illuminating provides an additional incident illumination for optically emphasizing surface defects which have no pronounced edge structures.

2. The device according to claim 1, wherein the electronic camera is selected from the group consisting of a linear array camera, a CCD cameras and a matrix cameras.

3. The device according to claim 1, wherein the means for illuminating comprises a ring light providing the dark-field illumination.

4. The device according to one of claim 1, wherein the rotatable means for holding the tubular sample to be inspected comprises two parallel rollers.

5. The device according to claim 4, wherein the means for illuminating comprises a transillumination set up providing the transmittent illumination, the transillumination unit set up facing the camera and underneath the two parallel rollers.

6. The device according to claim 5, wherein the transillumination unit consists of an electroluminescent panel.

7. The device according to claim 6, wherein the transillumination unit comprises an optical waveguide with a front mounted lens system.

8. The device according to claim 4, wherein the two paralell rollers are arranged such that an inside surface of the tubular sample is at a highest possible point in space above the two parallel rollers.

9. The device according to claim 8, wherein a gap between the two parallel rollers is freely selectable.

10. The device according to claim 4, wherein a diameter of each of the two parallel rollers is selectable such that said diameter is comparable to the diameter of the tubular sample.

11. The device according to claim 4, wherein the two parallel rollers have a predetermined coefficient of friction to avoid slippage between the tubular sample and the two parallel rollers.

12. The device according to claim 4, wherein the two parallel rollers are rotatable at different angular velocities to avoid slippage between the tubular sample and the rollers.

13. The device according to claim 4, wherein the tubular sample is drawable by a negative pressure onto a surface of the two parallel rollers to avoid slippage between the tubular sample and the rollers.

14. The device according to claim 4, wherein external suction is utilizable to avoid slippage between the tubular sample and the two parallel rollers.

15. The device according to claim 4, wherein surfaces of the two parallel rollers are structured such that a positive connection is established between the tubular sample and the two parallel rollers to avoid slippage between the tubular sample and the rollers.

16. The device according to claim 1, wherein the rotatable means for holding the tubular sample to be inspected grip an interior of the tubular sample at end surfaces of the sample.

17. The device according to claim 1, wherein the rotatable means for holding the tubular sample to be inspected grip an exterior of the tubular sample to be inspected at end surfaces of the sample.

18. The device according to claim 16, wherein the tubular sample to be inspected is grippable discontinuously by the rotatable means.

19. The device according to claim 1, wherein contours of the tubular sample contours and any existing defects of a surface of the tubular sample surface are automatically detected and evaluated.

20. The device according to claim 1, wherein the means for illuminating utilizes different wavelengths to illuminate the tubular sample.

21. The device according to claim 1, wherein the computer-based electronic image-processing system includes inspection software loaded with CAD data for manufacturing a structure of the tubular sample and is configured to determine a deviation between an actual and a nominal structure of the tubular sample.

22. The device according to claim 1, wherein a focus depth of the lens system is small in relation to a diameter of the tubular sample.

23. The device according to claim 1, further comprising:
an auto-focus system.

24. The device according to claim 1, wherein the lens system of the camera is positionable relative to surfaces of the tubular sample to be inspected.

25. The device according to claim 1, wherein the lens system includes a plurality of optical arrangements arranged parallel to each other.

26. The device according to claim 1, wherein the incident illumination is implementable as coaxial illumination.

27. The device according to one claim 1, further comprising:
a topography sensor for differentiating between elevations and depressions and measuring the elevations and depressions of the surface of the tubular sample.

28. The device according to of claim 1, further comprising:
a layer thickness sensor for differentiating between layer thicknesses and measuring the layer thicknesses.

29. The device according to claim 1, wherein the tubular samples to be inspected have a coating.

30. The device according to claim 1, wherein the tubular sample is a stent.

31. The device according to claim 1, wherein the incident illumination for optically emphasizing surface defects comprises vertical illumination.

32. A method for automatic illumination and inspection of tubular samples with a device having rotatable means for holding the tubular samples to be inspected, an electronic camera with an associated lens system, a computer-based electronic image-processing system, and means for illuminating a tubular sample to be inspected, the method comprising:
providing the means for illumination opposite from the electronic camera;
illuminating surfaces of the tubular sample simultaneously by a combination of dark-field and transmittent illumination; and
providing additional incident illumination to optically emphasize surface defects which have no pronounced edge structures.

33. The method according to claim 32, wherein the dark-field illumination is provided by a ring light.

34. The method according to claim 32, wherein the transmittent illumination is provided by a transillumination unit arranged opposite the camera and underneath the rotatable means.

35. The method according to claim 32, wherein the rotatable means for holding the tubular sample to be inspected comprises two parallel rollers.

36. The method according to claim 35, wherein the two parallel rollers are rotatable at different angular velocities to avoid slippage between the tubular sample and the two parallel rollers.

37. The method according to claim 35, wherein the sample is drawn by a negative pressure onto the surface of the rollers to avoid slippage between the tubular sample and the two parallel rollers.

38. The method according to claim 32, further comprising gripping, by the rotatable means, an interior of the tubular sample to be inspected at its end surfaces for holding the tubular sample during inspection.

39. The method according to claim 32, further comprising gripping, by the rotatable means, an exterior of the tubular sample to be inspected at its end surfaces for holding the tubular sample during inspection.

40. The method according to claim 32, wherein contours of the tubular sample and any existing defects of a surface of the tubular sample are automatically detected and evaluated.

41. The method according to claim 32, wherein the steps of illuminating utilizes different wavelengths to illuminate the tubular sample.

42. The method according to claim 32, further comprising entering CAD data for manufacturing a structure of the tubular sample into inspection software of the computer-based electronic image-processing system to determine a deviation between an actual and a nominal structure of the tubular sample.

43. The method according to claim 32, wherein the step of providing the means for illumination comprises providing a plurality of optical arrangements arranged parallel to each other.

44. The method according to claim 32, wherein the incident illumination is provided as coaxial illumination.

45. The method according to claim 32, wherein the tubular sample is a stent.

46. The method according to claim 32, wherein the incident illumination for optically emphasizing surface defects comprises vertical illumination.

* * * * *